(12) United States Patent
Wade et al.

(10) Patent No.: US 7,829,300 B2
(45) Date of Patent: Nov. 9, 2010

(54) METHOD OF MEASURING THE ACTIVITY OF G(ALPHA)I- OR G(ALPHA)O-COUPLED RECEPTORS USING $CA^{2+}$ INFLUX IN CELLS

(75) Inventors: Erik James Wade, Aachen (DE); Elke Janocha, Linnich (DE); Tieno Germann, Aachen (DE)

(73) Assignee: Gruenenthal GmbH, Aachen (DE)

( * ) Notice: Subject to any disclaimer, the term of this patent is extended or adjusted under 35 U.S.C. 154(b) by 34 days.

(21) Appl. No.: 12/336,025

(22) Filed: Dec. 16, 2008

(65) Prior Publication Data

US 2009/0136989 A1     May 28, 2009

Related U.S. Application Data

(63) Continuation of application No. 11/143,456, filed on Jun. 3, 2005, now abandoned, which is a continuation of application No. PCT/EP03/13510, filed on Dec. 4, 2003.

(30) Foreign Application Priority Data

Dec. 5, 2002   (DE)  ................ 102 56 947

(51) Int. Cl.
    *G01N 33/567*     (2006.01)
    *C07K 14/705*     (2006.01)

(52) U.S. Cl. .................. 435/7.2; 435/7.1; 435/7.21; 436/501

(58) Field of Classification Search .............. None
See application file for complete search history.

(56) References Cited

U.S. PATENT DOCUMENTS

2002/0051980 A1    5/2002   Witte et al.

FOREIGN PATENT DOCUMENTS

WO     WO 00/49416     8/2000

OTHER PUBLICATIONS

Gopalakrishnan S M et al., "A cell-based microarrayed compound screening format for identifying agonists of G-protein-coupled receptors". Annalytical Biochemistry, Academic Press, San Diego, CA, US Bd. 321, Nr. 2, Oct. 15, 2003, Seiten 192-201, XP004457157, ISSN: 0003-2697 das ganze Dokument.
Stables Jenny et al., "A bioluminescent assay for agonist activity at potentially any G-protein-coupled receptor" Analytical Biochemistry, Bd. 252, Nr. 1, 1997, Seiten 115-126, XP002274702, ISSN:003-2697, Zusammenfassung; Abbildungen 3, 5, 8.
Coward Peter et al.: "Chimeric G proteins allow a high-throughput signaling assay of Gi-coupled receptors" Analytical Biochemistry, Bd. 270, Jun. 1, 1999, Seiten 242-248, XP002274703, ISSN: 0003-2697, Zusammenfassung.
International Search Report dated Apr. 16, 2004 (8 pages).
Okajima et al. Synergism in cytosolioc $Ca^{30}$ mobilization between bradykinin and agonists for pertussis toxin-sensitive G-protein-coupled receptors in NG 108-15 cells. Apr. 1992, FEBS Letters 301(2):223-226.
Selbie et al. G protein-coupled-receptor cross-talk: the fine-tuning of multiple receptor-signaling pathways. Mar. 1998, TIPS 19:87-93.

*Primary Examiner*—John D Ulm
(74) *Attorney, Agent, or Firm*—Crowell & Moring LLP

(57) ABSTRACT

A method of measuring the activation or deactivation of G(alpha)i- or G(alpha)o-coupled receptors, and methods of identifying agonists or antagonists of such receptors.

33 Claims, 4 Drawing Sheets

METHOD OF MEASURING THE ACTIVITY OF G(ALPHA)I- OR G(ALPHA)O-COUPLED RECEPTORS USING CA²⁺ INFLUX IN CELLS

CROSS REFERENCE TO RELATED APPLICATIONS

This application is a continuation of U.S. patent application Ser. No. 11/143,456, filed Jun. 3, 2005, which is a continuation of international patent application no. PCT/EP2003/013510, filed Dec. 4, 2003, designating the United States of America, and published in German as WO 2004/051264 on Jun. 17, 2004, the entire disclosures of which are incorporated herein by reference. Priority is claimed based on Federal Republic of Germany patent application no. DE 102 56 947.9, filed Dec. 5, 2002.

BACKGROUND OF THE INVENTION

The present invention relates to a method of measuring the activation or deactivation of G(alpha)i-coupled or G(alpha)o-coupled receptors, and to methods of identifying agonists or antagonists of such receptors.

G-protein-coupled receptors (GPCR) are an extensive family of proteins which play an important role in signal transduction in cells. The term "GPCR" is derived from their association with a heterotrimeric complex of G(alpha), G(beta) and G(gamma) subunits. The G(alpha) subunits of the receptors involved in the synaptic transmission of signals can roughly be categorized on the basis of their function and coupling with the GPCRs. The members of the G(alpha)s family stimulate the activity of adenylate cyclases, while those of the G(alpha)i/o family inhibit the activity of adenylate cyclases. The proteins of the G(alpha)q and G(alpha)12/13 family are effective stimulators of the activity of phospholipase C(beta). However, these subtypes do not exhibit any action in respect of adenylate cyclase activity. A given GPCR usually interacts with only a single family of the G(alpha) proteins, although some exceptions to this rule are known.

The name G(alpha) proteins is derived from their ability to bind guanosine di- or tri-phosphate (GDP or GTP), which acts as a switch which regulates the activity and association of the G(alpha) protein with the GPCR and the G(beta)/G(gamma) subunits. GDP binds to G(alpha) proteins in their inactive state, in which they are present in non-covalent association with the G(beta)/G(gamma) subunits and a corresponding GPCR. GPCR activation leads to allosteric conformation changes in the receptor, leading to dissociation of the G-protein heterotrimer from the receptor and to dissociation of the bound GDP from the G(alpha) component. The intracellular concentrations of GTP usually exceed the concentrations of GDP by several orders of magnitude. The dissociation of GDP from the G(alpha) subunit therefore leads to binding of GTP. The binding of GTP to the G(alpha) subunit produces an allosteric conformation change which results in the dissociation of the G(alpha) subunit from the beta and gamma subunits and to activation of the effector functions of the alpha subunit. The beta and gamma constituents remain firmly connected with one another and therefore form a single functional unit. As soon as they are released from the complex with the G(alpha) subunit and from the GPCR, they execute various effector functions independently of the G(alpha) constituent. The described G-protein cycle is completed by hydrolysis of the GTP bound to the G(alpha) subunit by its intrinsic GTPase activity. As a result of this step, the G(alpha) subunit returns to the original state, which leads to reassociation with the beta/gamma subunits and finally to binding of the heterotrimer to the GPCR again.

Measurement of the activity of G(alpha)q-coupled receptors on the basis of measurement of the cytoplasmic $Ca^{2+}$ concentration, for example in living cells, with small, cell-membrane-permeable molecules, such as fluorescent dyes which change their fluorescent properties after binding of $Ca^{2+}$, is known in the art. These methods are based on the fact that G(alpha)q proteins activate phospholipase C(beta), which catalyses the cleavage of phosphotidylinositol-(4,5)-bisphosphate (PIP2) to inositol triphosphate (IP3) and diacylglycerol (DAG). In contrast to PIP2, which is an integral membrane lipid, IP3 is present in the cytosol in dissolved form. Accordingly, IP3 released by the action of phospholipase C(beta) can diffuse to IP3 receptor calcium channels of the endoplasmic reticulum (ER) and effect the release of $Ca^{2+}$ from the ER. The resulting increased cytoplasmic $Ca^{2+}$ concentration correlates directly with the activation of the GPCR, which is why measurement of the cytoplasmic $Ca^{2+}$ permits indirect measurement of receptor activation. Using such methods it is possible, for example, to evaluate potential ligands of the receptor in question with respect to their agonistic or antagonistic properties.

By contrast, measurement of the activity of G(alpha)i- or G(alpha)o-coupled receptors proves to be much more difficult. As discussed above, G(alpha)i and G(alpha)o subunits act on adenylate cyclase. A possible approach therefore consists in measuring the product of this enzyme, cyclic 3'-5'-adenosine monophosphate (cAMP). However, measurement of cAMP is expensive, time-consuming and is limited by a relatively small dynamic range of the test. In a further method, a chimeric G(alpha) protein is introduced into the cells, in which the interaction with the G(alpha)i- or G(alpha)o-coupled GPCR in question is retained, while the downstream effector action of the G(alpha) protein is changed from inhibition of adenylate cyclase to activation of phospholipase C(beta), so that determination of the GPCR activity is again made possible by measuring the cytoplasmic $Ca^{2+}$ (see Coward et al. (1999) Anal. Biochem. 270(2): 242-248). However, this technique requires an additional, time-consuming cloning step for the provision of the G(alpha) chimera, especially if stable transfectants are required. Furthermore, owing to the artificial nature of the chimera, artificial results that differ from the actual situation in vivo cannot be ruled out.

SUMMARY OF THE INVENTION

The object underlying the present invention is, therefore, to provide an improved method of measuring the activity of G(alpha)i- or G(alpha)o-coupled receptors.

It was also an object of the invention to provide a novel method of measuring the activity of G(alpha)i- or G(alpha)o-coupled receptors which overcomes the disadvantages of methods known in the prior art.

These and other objects have been achieved in accordance with the present invention by providing a The relates in particular to a method of measuring the activation of a G(alpha)i- and/or G(alpha)o-coupled receptor in cells that express at least one G(alpha)q-coupled receptor, which method comprises:

(a) simultaneously treating the cells with an amount (or concentration) of an agonist of the (at least one, i.e., in the case of a plurality, of any one of the plurality) G(alpha)q-coupled receptor such that a sub-threshold activity is obtained, and with an agonist of the G(alpha)i- and/or G(alpha)o-coupled receptor, and (b) measuring the cytoplasmic $Ca^{2+}$ concentration of the cells.

The measuring method according to the invention permits indirect measurement of the activity of G(alpha)i/o-coupled GPCRs on the basis of a synergistic interaction between activated G(alpha)q-coupled GPCRs and G(alpha)i/o-coupled GPCRs. In particular, phospholipase C(beta) (abbreviated to PLC(beta) hereinbelow) is activated in two separate phases. During the first phase, free G(beta)/G(gamma) subunits bring PLC(beta) to the plasma membrane, as a result of which the enzyme and its substrate (PIP2) are brought close together. During the second phase, G(alpha)q subunits activate the enzymatic activity of PLC(beta). Using an agonist of the G(alpha)q-coupled receptor, for example ATP or UTP, to initiate a specific sub-threshold activation of G(alpha)q receptors, the activity of G(alpha)i/o-coupled receptors can therefore be measured in a simple and effective manner.

In accordance with the invention, the amount or concentration of the agonist of the G(alpha)q-coupled receptor that produces a "sub-threshold" activity is especially that amount or concentration at which the ratio of the result of a measurement of the cytoplasmic $Ca^{2+}$ concentration of cells treated with a specific amount of an agonist of the G(alpha)q-coupled receptor to the result of the measurement of the cytoplasmic $Ca^{2+}$ concentration of cells treated with the same amount (or concentration) of the above-mentioned agonist of the G(alpha)q-coupled receptor and at the same time with an amount (concentration) of an agonist of a G(alpha)i- and/or G(alpha)o-coupled receptor that is sufficient for the complete activation thereof, is as small as possible, that is to say does not exceed about 1:3. Preferably, this ratio is not more than about 1:10, especially not more than about 1:20, particularly preferably it is minimal for the respective pair of agonists of the receptors. Of course, the above ratio of the measurement results can also be formed the other way round (that is to say, cytoplasmic $Ca^{2+}$ concentration after simultaneous treatment with an agonist of a G(alpha)q receptor and an agonist of the G(alpha)i/o-coupled receptor to cytoplasmic $Ca^{2+}$ concentration after treatment only with an agonist of a G(alpha)q-coupled receptor). In this case, the amount or concentration of the agonist that initiates a sub-threshold activity of the G(alpha)q-coupled receptor corresponds to the amount or concentration at which the ratio of the measurements of the cytoplasmic $Ca^{2+}$ concentrations is as large as possible, that is to say is not less than about 3:1, preferably at least about 10:1, especially at least about 20:1.

This means that the amount (concentration) of the agonist of the G(alpha)q-coupled receptor that produces a sub-threshold activity is the amount (concentration) at which maximum signal amplification possible is detected on measurement of the cytoplasmic $Ca^{2+}$ concentration, when the cells are treated simultaneously with the agonist of the G(alpha)q-coupled receptor and with the agonist of the G(alpha)i/o-coupled receptor in question, in comparison with a measurement of the $Ca^{2+}$ concentration obtained on treatment of the cells only with the same amount or concentration of the agonist of the G(alpha)q-coupled receptor. Because the cytoplasmic $Ca^{2+}$ concentration is a measure of the activity of phospholipase C(beta), the method according to the invention, and the determination of the amount of the agonist of the G(alpha)q-coupled receptor that produces a sub-threshold activity, can of course be carried out with the aid of any other suitable test for determining the activity of phospholipase C(beta).

The measuring method according to the invention is also especially suitable for identifying agonists of a given G(alpha)i- or G(alpha)o-coupled receptor. The present invention accordingly further provides such an identification method, which comprises (i) providing cells that express the G(alpha)i- and/or G(alpha)o-coupled receptor and at least one G(alpha)q-coupled receptor, and (ii) carrying out the above measuring method according to steps (a) and (b). In contrast to the measuring method according to the invention, of course, a (known) agonist of the G(alpha)i- or G(alpha)o-coupled receptor is not used in step (a), but a test substance whose effect on the GPCR in question is to be investigated is employed.

The measurement principle of the present invention can be used not only to measure the activation of G(alpha)i- or G(alpha)o-coupled receptors by corresponding agonists, but likewise to measure deactivation, or prevention of activation, owing to antagonists of these receptors. The present invention therefore provides a method of measuring the deactivation of a G(alpha)i- and/or G(alpha)o-coupled receptor in cells that express at least one G(alpha)q-coupled receptor, which method comprises the steps:

(A) simultaneously treating the cells with an amount (or concentration) of an agonist of the G(alpha)q-coupled receptor such that a sub-threshold activity is obtained, and with an amount (concentration) of an agonist of the G(alpha)i- and/or G(alpha)o-coupled receptor which is just sufficient for complete activation;

(B) measuring the cytoplasmic $Ca^{2+}$ concentration of the cells;

(C) simultaneously treating the cells with the same amount (or concentration) as in step (A) of the agonist of the G(alpha)q-coupled receptor, with the same amount (or concentration) as in step (A) of the agonist of the G(alpha)i- and/or G(alpha)o-coupled receptor and with an antagonist of the G(alpha)i- and/or G(alpha)o-coupled receptor;

(D) measuring the cytoplasmic $Ca^{2+}$ concentration of the cells; and (E) comparing the results from the measurements of steps (B) and (D).

The amount (or concentration) of the agonist of the G(alpha)q-coupled receptor that produces a sub-threshold activity is as defined above in respect of the method according to the invention for measuring the activation of a G(alpha)i- and/or G(alpha)o-coupled receptor.

According to the invention, it is also possible for the cells in step (C) to be treated first with the antagonist of the G(alpha)i- and/or G(alpha)o-coupled receptor and then, in a separate step, be treated simultaneously with the agonist of the G(alpha)q-coupled receptor and the agonist of the G(alpha)i- and/or G(alpha)o-coupled receptor.

If the measurement of the cytoplasmic $Ca^{2+}$ concentration in step (D) yields a smaller value than in step (B), then the receptor in question has been deactivated by the antagonist. Step (E) can therefore comprise forming the difference or a quotient of the measurement results from steps (B) and (D). By appropriately plotting these differences or quotients in dependence on the amount or concentration of the antagonist, characteristic values, for example inhibition constants, IC50 values, etc., can be determined for the receptor or the antagonist in question by methods known to a person skilled in the art. Of course, the same also applies to the agonists, in the case of concentration-dependent measurement series in respect of the above method of measuring the activation of a G(alpha)i- and/or G(alpha)o-coupled receptor.

The measuring method according to the invention for determining the deactivation of a G(alpha)i- and/or G(alpha)o-coupled receptor as a result of an antagonist can also be used advantageously within the scope of a method for identifying such antagonists. Such an identification method therefore comprises (I) providing cells that express the G(alpha)i- and/or G(alpha)o-coupled receptor and at least one G(alpha) q-coupled receptor, and (II) carrying out steps (A) to (E) according to the above measuring method. Of course, there is again used in step (C), instead of a known antagonist, a test substance whose antagonistic action in respect of the GPCRs in question is to be tested.

The above-defined amount or concentration of the agonist of the G(alpha)i- and/or G(alpha)o-coupled receptor that produces a sub-threshold activity is determined according to advantageous embodiments of the method according to the invention by an empirical procedure. For this purpose, the following steps are carried out:

(1) treating the cells with different amounts (or concentrations) of the agonist of the G(alpha)q-coupled receptor;
(2) measuring the cytoplasmic $Ca^{2+}$ concentration of the cells for each amount (concentration) of the agonist of step (1);
(3) simultaneously treating the cells with different amounts (or concentrations) of the agonist of the G(alpha)q-coupled receptor and with a constant amount (concentration) of the agonist of the G(alpha)i- and/or G(alpha)o-coupled receptor, which amount is sufficient for complete activation of the receptor;
(4) measuring the cytoplasmic $Ca^{2+}$ concentration of the cells for each amount (concentration) of the agonist of the G(alpha)q-coupled receptor of step (3); and
(5) comparing the results, in particular forming (calculating) the ratio of the measurements of steps (2) and (4) for in each case equal amounts (concentrations) of the agonist of the G(alpha)q-coupled receptor.

With the aid of the above procedure, the amount or concentration of the agonist of the G(alpha)q-coupled receptor that produces a sub-threshold activity is preferably established as that amount or concentration at which a ratio of the measuring results of steps (2) and (4) is obtained that is not more than about 1:3, preferably not more than about 1:10, especially not more than about 1:20. Of course, it is again possible to use the reciprocal value as the reference parameter, a ratio of not less than about 3:1, preferably at least about 10:1, more preferably at least about 20:1, accordingly indicating an amount (or concentration) of the agonist of this receptor that brings about a sub-threshold activity of the G(alpha)q-coupled receptor.

In addition to measurement of the activity/inhibition of G(alpha)i/o-coupled receptors on the basis of the above-described synergistic interaction with G(alpha)q-coupled receptors, the present invention additionally also provides corresponding methods which make use of a corresponding synergistic interaction between G(alpha)q-coupled and G(alpha)s-coupled receptors, between G(alpha)12/13-coupled and G(alpha)i/o-coupled receptors or between G(alpha)12/13-coupled and G(alpha)s receptors. According to the invention, therefore, corresponding methods are disclosed for measuring the activity/inhibition of G(alpha)s-coupled receptors on the basis of a synergistic interaction with G(alpha)q-coupled receptors. There are further disclosed according to the invention also corresponding methods for measuring the activity/inhibition of G(alpha)i/o-coupled receptors on the basis of a synergistic interaction with G(alpha)12/13-coupled receptors. Furthermore, the present invention relates also to corresponding methods for measuring the activity/inhibition of G(alpha)s-coupled receptors using a synergistic interaction with G(alpha)12/13-coupled receptors. In the mentioned methods of the present invention, the receptors and their agonists or antagonists mentioned in the above-defined method steps are replaced by the receptors and their agonists/antagonists that are to be measured and the receptors and their agonists that interact synergistically with those receptors to be measured.

The manner in which the cytoplasmic $Ca^{2+}$ concentration of the cells is measured is not limited in any way according to the invention. Appropriate measuring processes are known in the prior art. For example, suitable kits for measuring the cytoplasmic $Ca^{2+}$ concentration are available commercially, for example the FLIPR® Calcium Plus Assay Kit from Molecular Devices. Measurement of the cytoplasmic $Ca^{2+}$ concentration is usually carried out using $Ca^{2+}$-dependent dyes. This means that the dye in question changes its spectral properties in some way as a result of the binding of $Ca^{2+}$ ions, which is accordingly amenable to photometric detection. The "binding" of one or more $Ca^{2+}$ ions to the particular dye is not limited; often, however, it is complexing of one or more calcium ions by the dye molecule.

Due to their particular advantages, especially with regard to accuracy and sensitivity of the measurement, preference is given to fluorescent dyes, especially those that are small, cell-membrane-permeable molecules, for the determination of the cytoplasmic $Ca^{2+}$ concentration. These molecules therefore change their fluorescent properties when binding calcium ions. Particularly suitable $Ca^{2+}$-dependent fluorescent dyes for use in the method according to the invention are, for example, fluorescent dyes of the molecule families fura (e.g. fura-2, fura-4F, fura-5F, fura-6F, fura-FF, fura-red, mag-fura, bis-fura, such as bis-fura-2, especially cell-membrane-permeable derivatives of these compounds, such as their esters, e.g. the acetoxymethyl esters), indo (e.g. indo-1, indo-5F and mag-indo-1 and cell-membrane-permeable derivatives thereof, especially suitable esters, such as the acetoxymethyl esters, of these compounds), quin (e.g. quin-2 and quin-2 esters, such as quin-2-acetoxymethyl ester), coumarinbenzothiazoles (e.g. BTC and the ester derivatives thereof, especially BTC-acetoxymethyl ester), fluo (e.g. fluo-3, fluo-4, fluo-5F, fluo-4FF, fluo-5N and mag-fluo-4 and suitable esters of these compounds, such as the acetoxymethyl esters), calcium green (e.g. calcium green 1, 2 and 5N and suitable esters of these compounds, such as the acetoxymethyl esters), Oregon green (e.g. Oregon green 488 BAPTA-1, -2, -6F and -5N and suitable esters of these compounds, such as the acetoxymethyl esters), calcium orange, calcium crimson, magnesium green and suitable esters thereof, especially the acetoxy-methyl esters, rhod (e.g. rhod-2, -FF and -5N and suitable esters of these compounds, such as the acetoxymethyl esters) and X-rhod (e.g. X-rhod-1, -5F and FF and suitable esters of these compounds, such as the acetoxymethyl esters), which are all available commercially (Molecular Probes).

In the method according to the invention, the receptors to be analyzed, or the receptors with respect to which, in the case of test substances, an agonistic or antagonistic activity is to be determined, that is to say the particular G(alpha)i- or G(alpha)o-coupled receptor, but also the respective G(alpha)q-coupled receptor, can be expressed in the cells both endogenously and exogenously. In the latter case, the cells are therefore transfected with a nucleic acid construct which codes for the particular receptor(s) and ensures the expression of this or these receptor/receptors. The cells may either be transfected transiently for the temporary expression of the particular receptor, or it is possible to use a construct for stable integration into the genome of the particular cells, in order to ensure stable expression of the receptor. Of course, with regard to the expression of the corresponding receptors, any combinations, according to the desired property, of the above-described expression possibilities are possible according to the invention. It is thus possible, for example, to use cells that express both the G(alpha)q-coupled receptor and the particular G(alpha)i/o-coupled receptor endogenously. It is also possible, however, for only the G(alpha)q-coupled or only the "G(alpha)i/o-coupled receptor to be expressed endogenously by the cells, while the other receptor type is expressed exogenously on account of a transfection (transient or stable) with a corresponding nucleic acid construct, especially a vector suitable for expression. Of course, heterologous expression of both receptor types in the cells by means of the corresponding constructs is also possible.

Due to the possibility of the exogenous expression of receptors, especially of the particular G(alpha)i/o-coupled receptor, fragments, derivatives, alleles and mutants that are modified with respect to the wild-type receptor can also be expressed according to the invention and thus used in the methods according to the invention. For example, it is thus possible to investigate the activity of a G(alpha)i- or G(alpha)o-coupled receptor, which owing to a derivatisation or a mutation exhibits a modified association with respect to a particular agonist or antagonist, in respect of its activation or deactivation by the corresponding agonist or antagonist. The corresponding modification may, of course, be such that a stronger or weaker association with the ligand, i.e. with the agonist or antagonist, is produced.

The G(alpha)i- or G(alpha)o-coupled receptor is therefore not subject to any limitations according to the invention. Examples are opioid receptors (e.g. μ, κ, δ and ORL1), P2Y12, Edg family, GABA-B, muscarine-M2, -M4, dopamine-D2, -D3, -D4, histamine-H3, serotonin-H1 family, C3a, C5a, fMLP, CXCR1-5, CCR1-9, XCR1, CX3CR1, neuropeptide-Y1 to 6, somatostatin-Sst2, chemoattractant R-homologous molecule expressed on Th2 cells, prostaglandin-E type 3, adenosine-A1 and adenosine-A3 receptors.

According to the invention there are no limitations either regarding the G(alpha)q-coupled receptor. It is therefore possible to use both wild-type receptors and fragments, alleles, derivatives or mutants of G(alpha)q-coupled receptors, with the proviso that the particular fragment, allele, derivative or mutant is capable of binding an agonist and initiating the above-described dynamic interaction between the receptor systems on the basis of the particular G-proteins. There may be mentioned as examples of G(alpha)q-coupled receptors which can be used according to the invention, without implying any limitation, the receptors muscarine-M1, -M3, -M5, serotonin-H2, bombesin, cholecystokinin, neurokinin, prostaglandin-E type I, adenosine-A2B, P2Y1, P2Y2, P2Y4, P2Y6, P2Y11, calcitonin, mGluR1 receptors, angiotensin II receptor 1, protease activated receptor 1 and serotonin R. As mentioned above, it is, of course, also possible to use functional derivatives, alleles, fragments or mutants of these receptors.

Because of the above-described freedom in the choice of the receptors to be used or investigated in the method according to the invention, there is no limitation either regarding the agonists or antagonists to be used. According to the invention, an "agonist" is a substance that activates the particular receptor, while an "antagonist" inhibits the activation of the particular receptor, in particular is adapted to an inactive conformation of the receptor due to its structure. Agonists and antagonists of the particular receptors that can be used in the methods according to the invention can accordingly be selected from all possible classes of substance. Examples which may be mentioned include inorganic molecules, for example also ions that interact with receptors, small organic compounds and also biomolecules that have an agonistic or antagonistic action on the particular receptor, especially peptides, polypeptides, for example proteins, nucleic acids, lipids or saccharides, such as mono-, oligo- or poly-saccharides. Combinations of such molecules, which may be synthetic or naturally occurring, may likewise be agonists or antagonists of the receptors in question. As further examples of agonists of G(alpha)q-coupled receptors there may be mentioned nucleobases or nucleotides, such as, for example, adenosine, AMP, ADP, ATP, uridines, UMP, UDP, UTP, cytosine, CMP, CDP, CTP, guanosine, GMP, GDP, GTP, thymidine, TMP, TDP, TTP, inosine, IMP, IDP and ITP and also muscarine receptor agonists (e.g. muscarine, bethanechol, metocloprimide, pilocarpine and oxotremorine M). Examples of agonists of G(alpha)i- and/or G(alpha)o-coupled receptors are the known agonists of the above receptors, such as GRT0777S, Damgo, fentanyl, serotonin, morphines, such as morphine, buprenorphine etc. Antagonists of the mentioned G(alpha)i- or G(alpha)o-coupled receptors are likewise known to a person skilled in the art. One specific example is naloxone.

The particular combination of agonists and optionally antagonists to be used in the corresponding method depends on the particular receptors, inter alia the endogenous provision of the particular cells used with receptors of the classes in question or with other receptors, which may possibly likewise bind the agonist(s) or optionally antagonist(s) considered for use. If a particular agonist or optionally antagonist of a particular G(alpha)q-coupled receptor or of a G(alpha)i/o-coupled receptor is to be used, then that agonist or antagonist should preferably be used in combination with cells that do not express a receptor that likewise binds this agonist or antagonist, or the cells should preferably express only those other receptors that clearly bind the agonist or antagonist in question more weakly, i.e. that exhibit a clearly lower affinity for this agonist or antagonist. Preferably, the affinity for the particular agonist or antagonist to be used in the methods according to the invention, in relation to other receptors, in comparison with the G(alpha)q-coupled or G(alpha)i/o-coupled receptors in question, should be lower at least by a factor of about 3, more preferably at least by a factor of at least about 10, especially by a factor of at least about 20. Of course, this is also true for the case in which the G(alpha)q-coupled receptor agonist provided for use is also bound by the G(alpha)i/o-coupled receptor to be investigated and vice versa. These points of view also apply, of course, in relation to the above-defined antagonists of G(alpha)i/o-coupled receptors in view of a possible interaction with the G(alpha)q-coupled receptor.

There is no limit either regarding the cells to be used in the methods according to the invention, provided it is ensured that the cells express at least one G(alpha)q-coupled receptor in addition to the G(alpha)i/o-coupled receptor. Accordingly, cells of stable cell lines, primary cell cultures or tissue cells can be used in the methods according to the invention. Cell lines have the advantage that they can be genetically manipulated if necessary, in order, for example, to provide exogenous expression of a particular receptor or, if the cell line under consideration expresses one or more receptors endogenously or exogenously owing to a previous stable transfection, which could be disruptive in the combination that is to be used of agonists of the G(alpha)q-coupled receptor and of the G(alpha)i/o-coupled receptor or the antagonist of the latter receptors, in order to suppress or prevent the expression of such disruptive receptors by measures known to a person skilled in the art, for example prevention of translation or transcription, for example by means of antisense techniques or RNA interference techniques or by knockout processes. It is therefore possible according to the invention, by using the processes, especially genetic processes, known to a person skilled in the art, to provide a specific measuring or test system that is customized for the use in question as a method of measuring activation or inactivation or for identifying agonists or antagonists of G(alpha)i/o-coupled receptors.

As preferred examples of cell lines which can be used according to the invention there may be mentioned any eukaryotic cell lines, especially mammalian cell lines, for example CHO (e.g. CHO K1), HEK293, THP-1, SH-SY5Y, Jurkat, HeLa, L cells, A-10, Cos-7, NIH 3T3, ECV304, RBL, UMR 106, PC3 GH3, PC1 and IMR-32. According to a further preferred embodiment of the methods according to the invention, because of the particular endogenous expression of one or more specific G(alpha)q-coupled receptors, particular combinations of cell line/agonist of the G(alpha)q-coupled receptor/receptors are preferably used. For example, in the case of HEK293 cells there is preferably used ATP (for sub-threshold stimulation of the P2Y1 or P2Y2 receptors), muscarine (for sub-threshold stimulation of the M1 receptor) and/or somatostatin (for sub-threshold stimulation of the somatostatin receptor), in order to effect sub-threshold stimulation of the particular G(alpha)q-coupled receptor/receptors. Similarly, in the case of CHO-K1 cells, ATP and/or UTP is preferably used in order to cause sub-threshold stimulation of the P2Y2 receptor endogenously present in these cells as the G(alpha)q-coupled receptor. The above circumstances apply in the case of stimulation of endogenously expressed receptors. However, it is of course possible in principle for a person skilled in the art, using standard molecular/cell biological techniques, to express any desired combination of receptors heterologously in a chosen cell (optionally with elimination or down-regulation of the expression of one or more receptors that are present endogenously and may possibly otherwise be disruptive) in order thus to be able to use a combination of receptor(s)/receptor agonist(s) customised for particular requirements.

When $Ca^{2+}$-dependent dyes are used, especially fluorescent dyes, measurement of the cytoplasmic $Ca^{2+}$ concentration can be carried out in a simple manner by photometry. Various measuring devices are available commercially for this purpose, for example Fluoroscan (Labsystems) or FLIPR (Molecular Devices). With the aid of such measuring systems, and furthermore with the use of suitable pipetting devices, culture devices, HPLC components, especially pumps, valves, etc., known to a person skilled in the art, and with the assistance of data processing systems and programs known to a person skilled in the art, especially for acquiring, storing and evaluating the measuring results, the methods according to the invention can, of course, be in semi- or fully automated form and, moreover, can be carried out with very different throughput speeds, for which reason, for example, high throughput screening (HTS) applications are also possible with the measuring and identification methods according to the invention.

A preferred field of application of the methods according to the invention is the measurement of the deactivation/activation of G(alpha)i/o-coupled receptors which are involved with signal formation, transduction and/or processing of pain sensations. Accordingly, the identification method according to the invention for agonists or antagonists of G(alpha)i/o-coupled receptors is used, for example, in the screening of test substances in the case of G(alpha)i/o-coupled receptors associated with pain sensations. Further fields of application are the screening of test substances in the case of G(alpha)i/o-coupled receptors associated with immunological disorders or diseases (here, for example, the receptors CXCR, CCR, XCR1 and CX3R) and neurodegenerative diseases, for example Parkinson's (here, for example, the receptors of the dopamine family).

BRIEF DESCRIPTION OF THE DRAWINGS

The invention will be described in further detail hereinafter with reference to illustrative embodiments and the accompanying drawing figures in which.

DETAILED DESCRIPTION

Figure 1A:
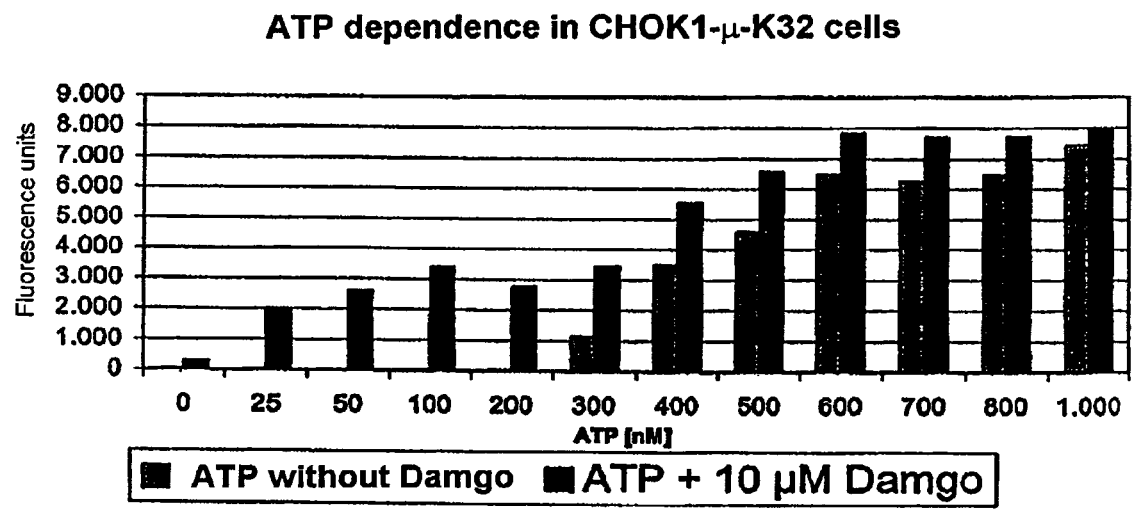
FIGS. 1 through 6 are graphs showing the relative fluorescence intensity depending on the concentration of specific agonists or antagonists of G-coupled cell receptors. The relative fluorescence intensity is a direct measure of the $Ca^{2+}$ concentration owing to the use of a $Ca^{2+}$-dependent fluorescent dye (Fluo-4).

FIG. 1A is a graph showing the fluorescence intensity (as a relative unit) in the case of the cell line CHOK1-μ-K32 at different ATP concentrations in the range from 0 to 400 nM. It is shown that in the absence of DAMGO (grey bar), a μ opioid receptor agonist, a clear fluorescence signal of more than 1000 relative units is measured only with the addition of 300 nM ATP, while at 100 nM the measured fluorescence intensity is smaller by a factor of more than 100. In the presence of 10 μM DAMGO (black bar), but without ATP, a relatively small fluorescence signal of about 300 relative units is observed. This signal is substantially intensified in the presence of 25 nM ATP. At these ATP concentrations, as discussed above, only a very slight fluorescence signal was obtained when no DAMGO was present. With increasing concentrations of ATP (300 nM and above), the strength of the DAMGO-induced signal decreases, because ATP alone is capable, at these concentrations, of causing comparable signal intensities. As is shown by a comparison of the bars for 100 nM ATP in FIG. 1A, the greatest signal amplification is obtained at this ATP concentration as a result of the action of DAMGO. This ATP concentration (100 nM) was therefore used in the experiments, the results of which are described in FIGS. 2 to 6.

Figure 1B:
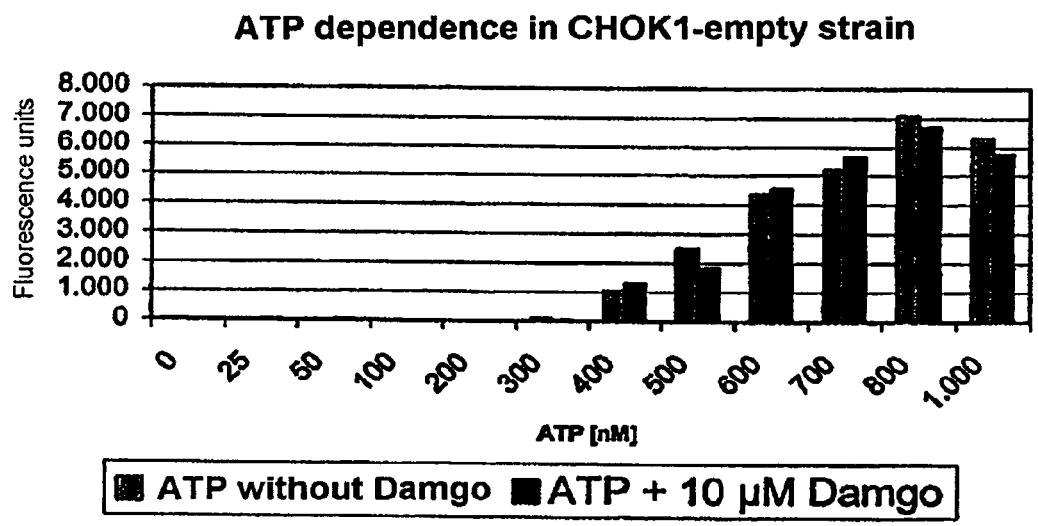

FIG. 1B is a graph showing the fluorescence intensity in the case of the cell line CHOK1-empty (mock) strain under the same conditions as FIG. 1A. At a concentration of 300 nM and above, ATP triggers, through the endogenous P2Y2 receptor, a fluorescence signal, which is not affected by DAMGO. A fluorescence signal in the sub-threshold range is not present, because the μ opioid receptor in these cells is missing and a synergism cannot occur.

Figure 2:
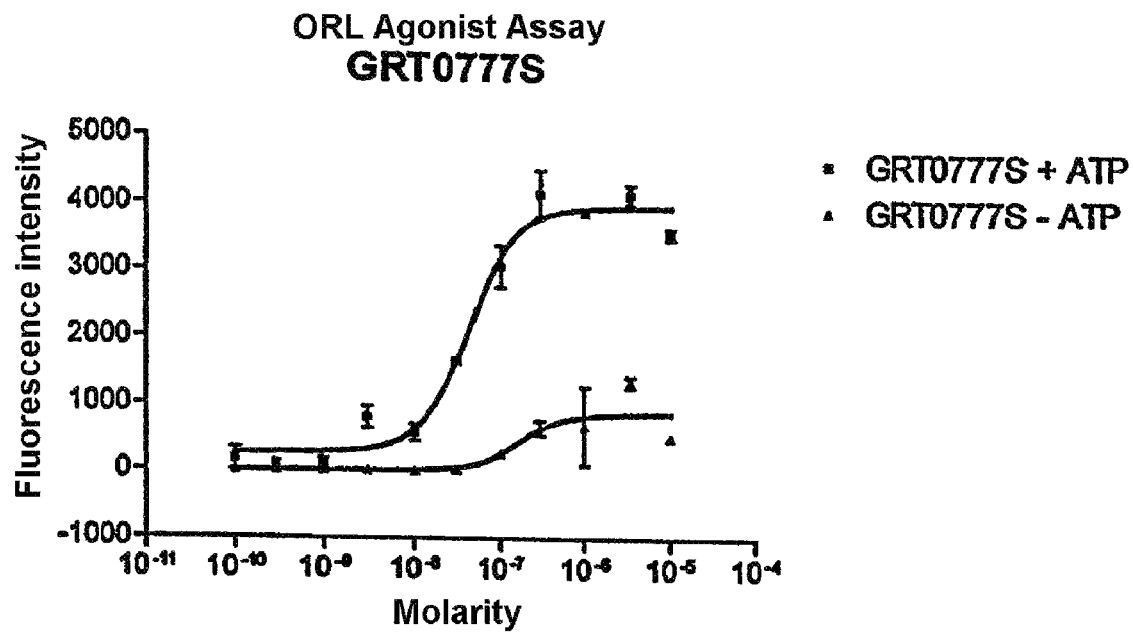

FIG. 2 is a graph showing that the presence of the agonist of the G(alpha)q-coupled receptor (ATP) is necessary to produce a clear fluorescence signal. Cells that express ORL1 stably (cell line CHOK1-ORL-K66) were used in this case, but the results for the μ-receptor-expressing cells under the same conditions are similar. GRT0777S produces a weak signal with an increasing concentration in the absence of ATP (▲). In the presence of 100 nM ATP, the measurable signal is clearly intensified at GRT0777S concentrations of more than $10^{-9}$ M (■). Moreover, the variability of the measurement results (see the deviations indicated for each measuring point in the figure) between independent experiments under the same conditions is lower when GRT0777S is used in the presence of 100 nM ATP. Accordingly, the activation of the G(alpha)i/o-coupled receptor by its agonist can be measured reliably in the presence of the suitable sub-threshold concentration of the agonist of a G(alpha)q-coupled receptor. Furthermore, the increased signal strength also permits the quantitative determination of the receptor activation in the suboptimal range, which leads to a five-fold reduction of the estimated IC50 value ($4.2 \times 10^{-8}$ M instead of $1.7 \times 10^{-7}$ M). The IC50 value of $4.2 \times 10^{-8}$ M determined with the aid of the method according to the invention is accordingly markedly closer to the data determined by means of receptor binding studies ($Ki = 4.0 \times 10^{-9}$).

Figure 3:
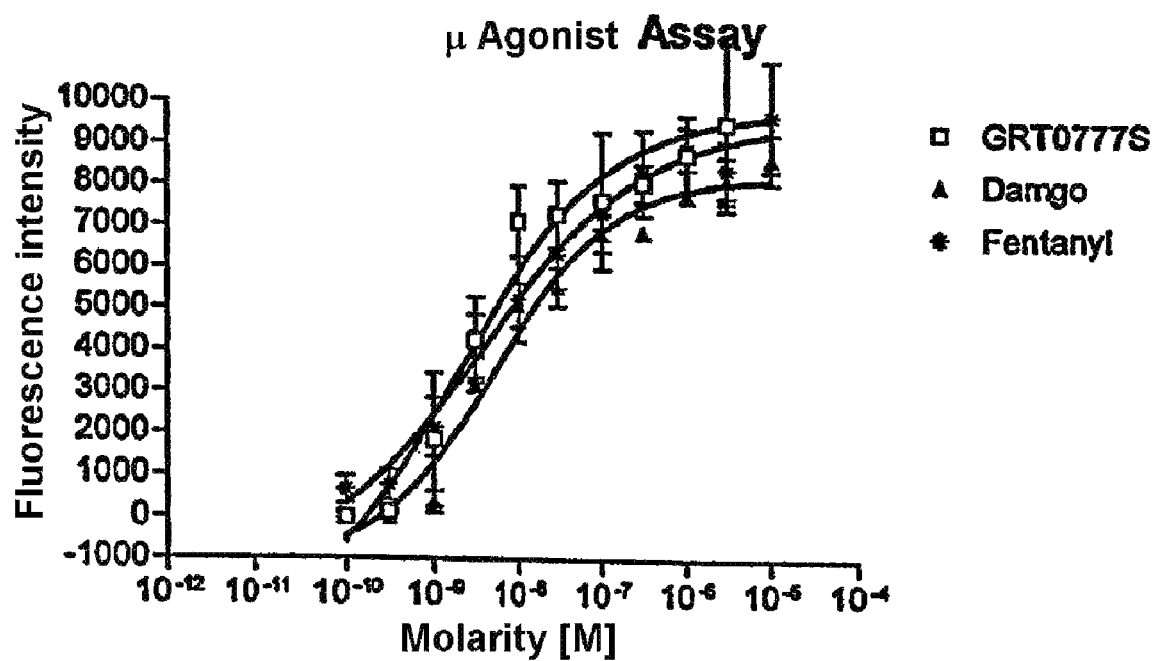

FIG. 3 is a graph showing the fluorescence intensity of CHOK1-μ-K32 cells in dependence on the added concentration of the μ-receptor agonist GRT0777S (□), DAMGO (▲) and fentanyl (*), in each case in the presence of 100 nM ATP. The average values of in each case 3 independent measurements are shown, the standard deviations being indicated. Conventional dose-response curves are found for all three receptor agonists. The very similar measured values of all three receptor agonists is due to the fact that all three substances exhibit similar binding affinities to the μ opioid receptor (Ki between 16 and 24 nM). When the same test was carried out on non-transfected CHOK1 cells, none of the μ-receptor agonists used gave a fluorescence signal above the background (not shown).

Figure 4A:
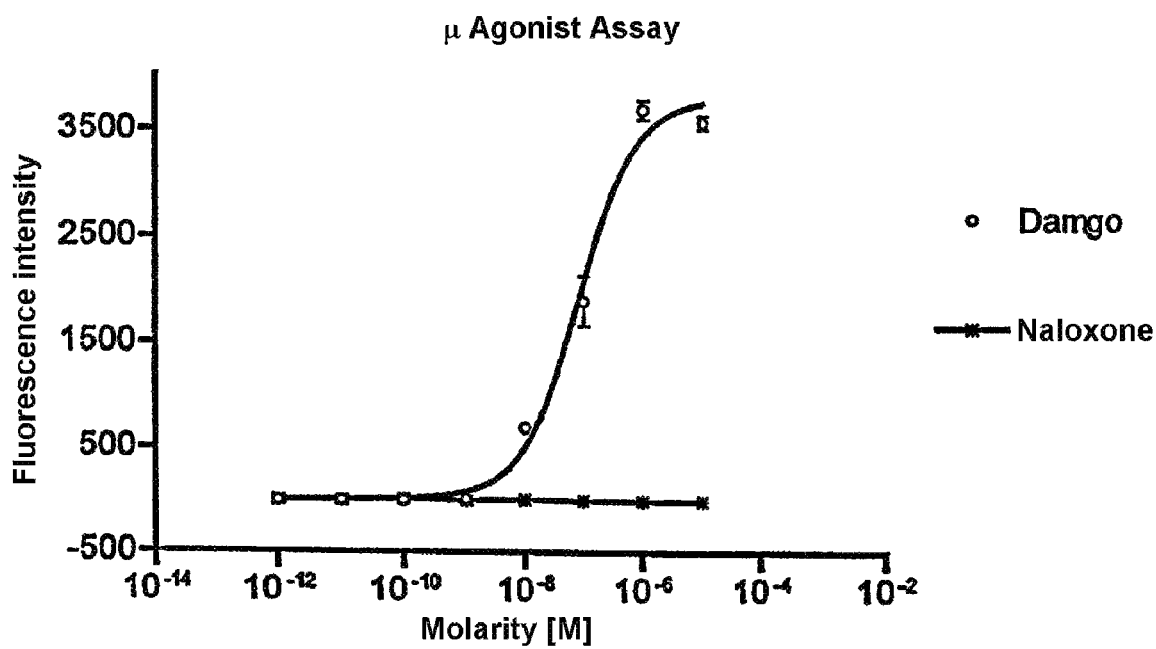

FIG. 4A is a graph showing the fluorescence intensity in the case of CHOK1-μ-K32 (express the μ opioid receptor) in dependence on various concentrations of the μ-agonist Damgo (○) or of the μ-antagonist naloxone (*), in each case in the presence of 100 nM ATP. While Damgo, as already established in the experiments according to FIG. 3, produces a conventional dose-response curve of the fluorescence intensity, naloxone, as expected, is unable to produce any fluorescence intensity above the background.

Figure 4B:
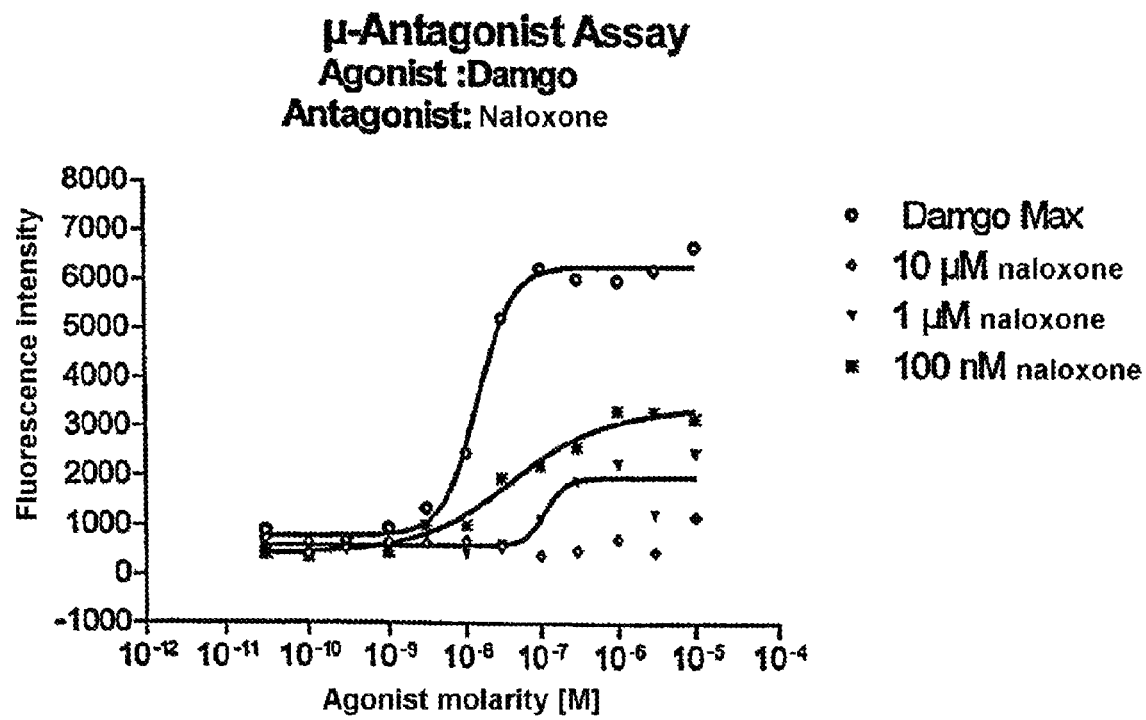

FIG. 4B is a graph showing an experiment corresponding to FIG. 4A, the fluorescence intensity in dependence on the added concentration of Damgo in the presence of 100 nM ATP, in each case for different concentrations of the μ-receptor antagonist naloxone. The experiment was carried out without naloxone (○), in the presence of 100 nM naloxone (*), 1 μM naloxone (▼) and 10 μM naloxone (◇). When both Damgo and naloxone were added together (in the presence of 100 nM ATP), the signal produced by Damgo is reduced in a dose-dependent manner by the antagonist naloxone. Therefore, the method according to the invention can be used to detect not only agonists but also antagonists in respect of a given G(alpha)i/o-coupled receptor. Furthermore, the large dynamic range of the test permits the detection of even relatively weak antagonists.

Figure 5:
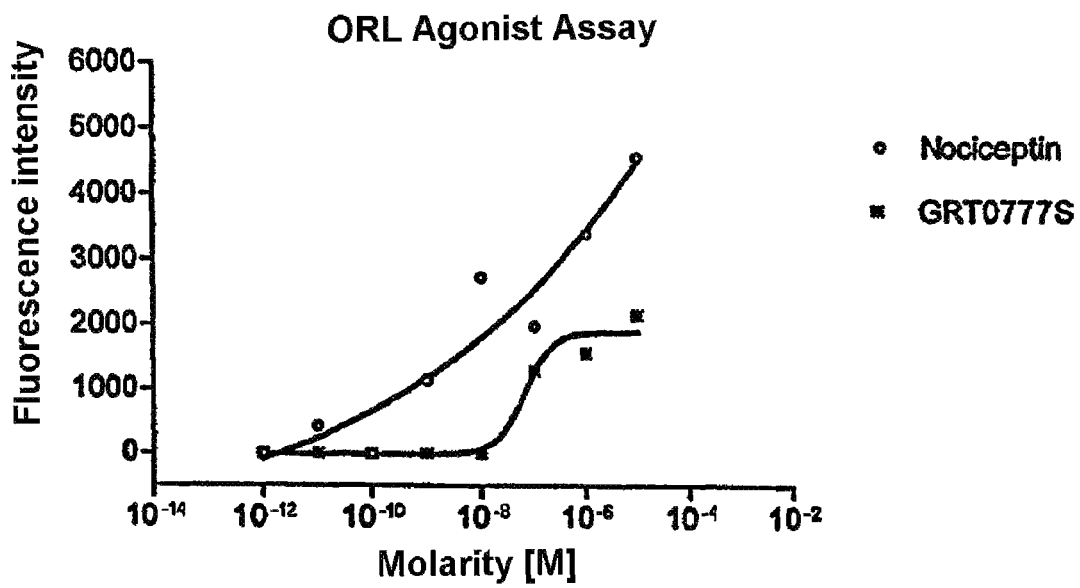

FIG. 5 shows the fluorescence intensity in cells of the cell line CHOK1-ORL-K66, which stably express the ORL1 opioid receptor. The cells were treated either with different concentrations of GRT0777S (*) or nociceptin (○), in each case in the presence of 100 nM ATP. Both GRT0777S and the peptide nociceptin (Orphanin FQ) exhibit their agonistic properties towards the ORL-1 receptor, while non-transfected cells do not produce a signal (not shown). Therefore, the synergistic principle, underlying the test according to the invention, between the G(alpha)q-coupled receptor and the G(alpha)i/o-coupled receptors is independent of the particular receptor because, as shown in FIGS. 1 to 4, the signal amplification is detected both in the case of the μ opioid receptor and (FIG. 5) in the case of the ORL-1 opioid receptor.

Figure 6:
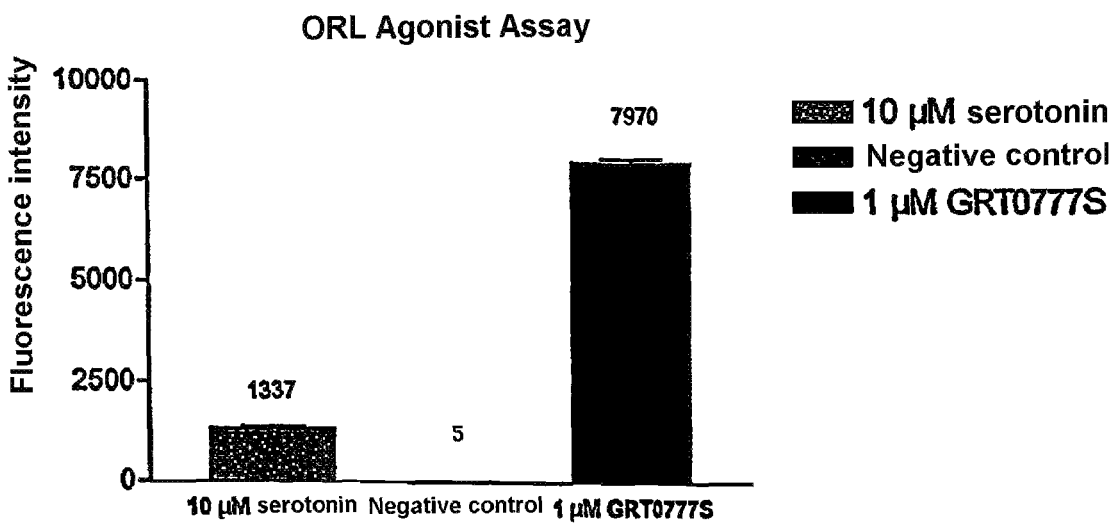

FIG. 6 demonstrates that the measuring principle underlying the present invention can also be used to investigate endogenously expressed G(alpha)i/o-coupled receptors. For this purpose, CHO cells, which overexpress the ORL1 receptor, were used as positive control. Cells treated with ATP alone show no significant signal (negative control). Cells treated with 1 μM GRT0777S, on the other hand, exhibit a markedly increased $Ca^{2+}$ concentration, as shown by the mean fluorescent intensity of 7970 relative units. However, CHO cells endogenously express a further G(alpha)i/o receptor, namely the 5HT1B receptor. If the cells are treated with serotonin, the natural ligand of the 5HT-1B receptor endogenously expressed by the CHO cells, in the presence of 100 nM ATP (serotonin concentration: 10 μM), a fluorescence intensity of on average 1337 relative units, and accordingly a clear signal, is measured. The measurement results shown in FIG. 6 in each case constitute the mean value of four independent measurements. Although the $Ca^{2+}$ concentration brought about by serotonin is relatively small compared with the signal produced by GRT0777S, this was expected in the present control experiment because the ORL1 receptor expressed by the CHOK1-ORL-K66 cells is present in a much greater copy number than the endogenously expressed serotonin receptor. A similar activation by serotonin is observed in non-transfected CHOK1 cells, while GRT0777S is not capable of triggering a signal in those cells for lack of an expressed ORL1 receptor (not shown).

In summary it has been possible to show by the experiments described in the above Figures that the combination of a G(alpha)q-dependent stimulus, here ATP in respect of the P2Y2 receptor, with stimulation of a G(alpha)i/o-coupled receptor permits the sensitive and accurate measurement of the activation of the G(alpha)i/o-coupled receptor in question by an agonist of that receptor, or the prevention of the activation of a G(alpha)i/o receptor on account of the action of an antagonist of that receptor. It has been shown that the measurement principle according to the invention permits the investigation of artificially expressed receptors, here the μ opioid receptor and the ORL1 receptor, as well as the investigation of endogenously expressed receptors, here the 5HT-1B receptor.

The following Examples are intended to illustrate the present invention in greater detail without limiting its scope.

EXAMPLE 1

Materials

The following materials were used for all the Examples.
Biocoat PDL 96-well plates Black No. 356640 from Becton-Dickinson
75 $cm^2$ bottles from Sarstedt
DMSO: Sigma
Fluo-4-AM-ester: Molecular Probes F14201
Probenecid: Molecular Probes
HBSS buffer: Invitrogen
HEPES: Sigma
Zeocin (for selection of the cells): Invitrogen
Cell culture medium: Ham's F12 (Gibco No.: 21765029), 10% FCS (PAA),
18 μg/ml L-proline (Sigma), 180 μg/ml zeocin (Invitrogen)
HBSS 1× without phenol red (Gibco No.: 140254-050), 2.5 mM Probenicid
(Molecular Probes), 20 mM HEPES (Sigma)

Cytoplasmic $Ca^{2+}$ Measurement

The cytoplasmic $Ca^{2+}$ concentration was measured in all the Examples using the FLIPR Calcium Plus Assay Kit and a corresponding FLIPR device from Molecular Devices, according to the manufacturer's instructions.

In brief, on the day preceding the experiment, the cells to be measured were plated out in a suitable 96-well cell culture plate, in a density of 25,000 cells per well, in a volume of 100 μl of the appropriate medium. Cell culture plates from Becton-Dickinson (order no. 66440) coated with poly-D-lysine were used for the test. On the day of the test, the cells were loaded with fluo-4. To that end, a vial of fluo-4 was dissolved in 23 μl of DMSO and 23 μl of Pluronic F 127. 42 μl of the solution were added to 21 ml of HBSS (+Probenecid and Hepes). 50 μl of this solution per well were added to the cells, the plates being incubated, for loading, for 30 minutes at 37° C., 5% $CO_2$, 98% relative humidity. In order to remove excess loading solution, the plates were washed three times with 200 μl of HBSS in a washing device for 96-well plates. This was followed by a dispension step, in which in each case 100 μl of HBSS were added to the cells. The plates were then left to stand in the dark, at room temperature, for at least 15 minutes.

When the FLIPR device had been switched on at about ½ hour before the start of the test, the appropriate FLIPR program was carried out.

A distinction is made between an agonist test (one addition) and an antagonist test (two additions). The substances to be tested were present in a higher concentration according to the dilution in the test. Depending on the test, the "cell plates" and "drug plates" were brought into the supply position or into the appropriate measuring position in the FLIPR. Before each measurement, the loading of the cells was checked by a brief measurement using the appropriate "snapshot" function. The program for the actual measurement (in the present case excitation at 488 nm, emission at from 510 to 570 nm) was started.

Calibration of the FLIPR measuring device was carried out once weekly using a calibration plate.

Determination of the Amount of an Agonist Required for the Sub-Threshold Activity of a G(alpha)q-coupled Receptor As model system for carrying out the measuring principle according to the invention there were used CHO K1 cells which, for the expression of G(alpha)i- or G(alpha)o-coupled opioid receptors (μ or ORL1 receptor), had been stably transfected with corresponding constructs using Lipofektamin 2000. CHO K1 cells endogenously express two receptors for ATP, P2Y2 and P2x7. P2Y2 is a G(alpha)q-coupled receptor whose affinity for ATP and UTP is comparable. P2X7 is a non-selective ion channel which does not bind UTP. This receptor binds ATP about 100 times more weakly than the G(alpha)q-coupled receptor P2Y2. Therefore, the signals measured here ($Ca^{2+}$ concentration) in the considered concentration ranges of the receptor agonist are dependent solely on the P2Y2 receptor.

In order to determine the amount or concentration of ATP suitable for measurement of the activity of the exogenously expressed opioid receptors, fluorescence measuring series were carried out with CHO-μ-K32 cells (stable expression of the μ opioid receptor) and different ATP concentrations (FIG. 1A, light bars, ATP without DAMGO). Only at a concentration at and above 300 nM ATP on its own is a change in the fluorescence detectable.

The experiment was repeated with the same ATP concentrations but in the presence of DAMGO, an agonist of the μ opioid receptor (FIG. 1A, dark bars, ATP+10 μM DAMGO). The greatest signal intensification (amplification) was obtained at 100 nM ATP. The following experiments were therefore carried out at that ATP concentration.

The same experiment was carried out on the CHO-K1 cells, without the stably transfected μ opioid receptor (so-called CHOK1 empty (mock) strain) (FIG. 1B). In the absence of the μ opioid receptor, no signal intensification (amplification) was observed in the sub-threshold range, which demonstrates the necessity of the μ opioid receptor for the synergistic effects. Without a corresponding receptor, DAMGO has no significant effect on the signal caused by ATP. This shows that the DAMGO-dependent effects are not mediated by an endogenous receptor.

EXAMPLE 2

Measurement of the Activation of G(alpha)i/o-Coupled Receptors by Different Agonists The activation of the μ receptor by the agonists GRT0777S, Damgo and fentanyl was measured, typical dose-response curves being obtained in the measured concentration range (10 μM to 0.1 nM) (FIG. 3).

The activation of the ORL1 receptor in the case of correspondingly stably transfected CHO K1 cells (CHOK1-ORL-K66) by GRT0777S (FIG. 2) or by the peptide antagonist nociceptin/Orphanin FQ (FIG. 5) (in each case in the presence of 100 nM ATP) gave the expected dose-response curves at the $Ca^{2+}$ concentrations measured by means of fluorescence, while a comparison test with GRT0777S without the addition of ATP (FIG. 2) caused only a very weak signal. The measuring principle according to the invention is therefore independent of the particular receptor or agonist. On the other hand, the presence of the agonist of the G(alpha)q-coupled receptor is necessary.

EXAMPLE 3

Measurement of the Deactivation of G(alpha)i/o-Coupled Receptors by Antagonists

The measuring principle according to the invention is also suitable for determining the inhibition of the activation of G(alpha)i/o-coupled receptors by corresponding antagonists.

In the case of the μ opioid receptor, CHO K1 cells (CHOK1-μ-K32), which stably express this receptor, were for this purpose first treated with the receptor agonist Damgo and 100 nM ATP or with the receptor antagonist naloxone and 100 nM ATP (FIG. 4A). Damgo showed the expected dose-response curve, while naloxone alone did not produce any signals.

If, however, Damgo was used together with naloxone, the signal caused by Damgo was diminished in dependence on the naloxone concentration, here over a range of three orders of magnitude, 100 nM to 10 μM naloxone (FIG. 4B).

EXAMPLE 4

Measurement of the Activation of Endogenously Expressed G(alpha)i/o-Coupled Receptors Because CHO K1 cells endogenously express not only the G(alpha)q-coupled ATP (or UTP) receptor P2Y2 but also the G(alpha)i/o-coupled serotonin receptor 5HT-1B, these cells (CHOK1-ORL-K66) were used to demonstrate that the synergistic measuring principle of the present invention is also suitable for measuring the activation of endogenously expressed receptors.

To that end, the cells were treated only with 100 nM ATP (negative control), with 100 nM ATP plus 1 μM GRT0777S (positive control) and with 100 nM ATP plus 1 μM serotonin. Compared with the negative control, the addition of the 5HT-1B agonist serotonin produced a marked signal intensification in the fluorescence measurement (FIG. 6).

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A method of measuring the activation of a G(alpha)i- and/or G(alpha)o-coupled receptor in cells that express at least one G(alpha)q-coupled receptor, said method comprising:
   (a) simultaneously treating the cells with an amount of an agonist of the G(alpha)q-coupled receptor such that a sub-threshold activity is obtained, and with an agonist of the G(alpha)i- and/or G(alpha)o-coupled receptor, and
   (b) measuring the cytoplasmic $Ca^{2+}$ concentration of the cells,
wherein the amount of the agonist of the G(alpha)q-coupled receptor that produces a sub-threshold activity is that amount at which the ratio of:
   (i) the result of the measurement of the cytoplasmic $Ca^{2+}$ concentration of the cells on treatment with an amount of the agonist of the G(alpha)q-coupled receptor
to
   (ii) the result of the measurement of the cytoplasmic $Ca^{2+}$ concentration of the cells on simultaneous treatment of the cells with the same amount of the agonist of the G(alpha)q-coupled receptor and an amount of an agonist of the G(alpha)i- and/or G(alpha)o-coupled receptor that is sufficient for complete activation,
does not exceed about 1:20.

2. A method of identifying agonists of a G(alpha)i- and/or G(alpha)o-coupled receptor, said method comprising:
   (i) providing cells that express the G(alpha)i- and/or G(alpha)o-coupled receptor and at least one G(alpha)q-coupled receptor; and
   (ii) carrying out steps (a) and (b) of the method according to claim 1, wherein a test substance, whose activity in respect of the G(alpha)i- and/or G(alpha)o-coupled receptor is to be tested, is used in step (a) as the agonist of the G(alpha)i- and/or G(alpha)o-coupled receptor.

3. A method according to claim 1, wherein before step (a) the amount of the agonist of the G(alpha)q-coupled receptor that gives a sub-threshold activity is determined by:
   (1) treating the cells with different amounts of the agonist of the G(alpha)q-coupled receptor;
   (2) measuring the cytoplasmic $Ca^{2+}$ concentration of the cells for each amount of the agonist of step (1);
   (3) simultaneously treating the cells with different amounts of the agonist of the G(alpha)q-coupled receptor and with a constant amount of the agonist of the G(alpha)i- and/or G(alpha)o-coupled receptor sufficient for complete activation of the receptor;
   (4) measuring the cytoplasmic $Ca^{2+}$ concentration of the cells for each amount of the agonist of the G(alpha)q-coupled receptor of step (3); and
   (5) comparing the results of the measurements of steps (2) and (4) for equal amounts of the agonist of the G(alpha)q-coupled receptor.

4. A method according to claim 3, wherein step (5) comprises calculating a ratio from the results of the measurements of steps (2) and (4).

5. A method according to claim 4, wherein the amount of the agonist of the G(alpha)q-coupled receptor is that amount at which a ratio of the result of the measurement of step (2) to the result of the measurement of step (4) of not more than about 1:20 is obtained.

6. A method according to claim 1, wherein the measurement of the cytoplasmic $Ca^{2+}$ concentration is carried out using a $Ca^{2+}$-dependent dye.

7. A method according to claim 6, wherein the dye is a fluorescent dye.

8. A method according to claim 7, wherein the fluorescent dye is selected from the group consisting of molecules of the families fura, indo, quin, coumarinbenzothiazoles, fluo, calcium green, Oregon green, calcium orange, calcium crimson, magnesium green, rhod and X-rhod.

9. A method according to claim 1, wherein the G(alpha)i- or G(alpha)o-coupled receptor is selected from the group consisting of opioid receptors, P2Y12, receptors of the Edg family, GABA-B, muscarine-M2, -M4, dopamine-D2, -D3, -D4, histamine-H3 receptors, receptors of the serotonin-H1 family, C3a, C5a, fMLP, CXCR1-5, CCR1-9, XCR1, CX3CR1, neuropeptide-Y1 to 6, somatostatin-Sst2 receptors, chemoattractant R-homologous molecule expressed on Th2 cells, prostaglandin-E type 3, adenosine-A1 and adenosine-A3 receptors.

10. A method according to claim 1, wherein the G(alpha)q-coupled receptor is selected from the group consisting of muscarine-M1, -M3, -M5, serotonin-H2, bombesin, cholecystokinin, neurokinin, prostaglandin-E type I, adenosine-A2B, P2Y1, P2Y2, P2Y4, P2Y6, P2Y11, calcitonin, mGluR1 receptors, angiotensin II receptor 1, protease activated receptor 1 and serotonin R.

11. A method according to claim 1, wherein at least one of the G(alpha)i-coupled receptor, the G(alpha)o-coupled receptor and the G(alpha)q-coupled receptor is expressed endogenously by the cells.

12. A method according to claim 1, wherein the cells have been transfected with a nucleic acid construct for expression of at least one receptor selected from the group consisting of the G(alpha)i-coupled receptor, the G(alpha)o-coupled receptor and the G(alpha)q-coupled receptor.

13. A method according to claim 1, wherein the cells are selected from the group consisting of stable cell lines, primary cell cultures and tissue cells.

14. A method according to claim 13, wherein the cell line is selected from the group consisting of CHO, HEK293, THP-1, SH-SY5Y, Jurkat, HeLa, L cells, A-10, Cos-7, NIH 3T3, ECV304, RBL, UMR 106, PC3, GH3, PC1 and IMR-32.

15. A method according to claim 1, wherein the agonist of the G(alpha)q-coupled receptor is selected from the group consisting of adenosine, AMP, ADP, ATP, uridine, UMP, UDP, UTP, cytosine, CMP, CDP, CTP, guanosine, GMP, GDP, GTP, thymidine, TMP, TDP, TTP, inosine, IMP, IDP and ITP and muscarine receptor agonists.

16. A method according to claim 1, wherein the agonist of the G(alpha)i- and/or G(alpha)o-coupled receptor is selected from the group consisting of GRT0777S, Damgo, fentanyl, serotonin and morphines.

17. A method of measuring the deactivation of a G(alpha)i-and/or G(alpha)o-coupled receptor in cells that express at least one G(alpha)q-coupled receptor, said method comprising:
   (A) simultaneously treating the cells with an amount of an agonist of the G(alpha)q-coupled receptor such that a sub-threshold activity is obtained, and with an amount of an agonist of the G(alpha)i- and/or G(alpha)o-coupled receptor which is just sufficient for complete activation;
   (B) measuring the cytoplasmic $Ca^{2+}$ concentration of the cells;
   (C) simultaneously treating the cells with the same amount as in step (A) of the agonist of the G(alpha)q-coupled receptor, with the same amount as in step (A) of the agonist of the G(alpha)i- and/or G(alpha)o-coupled receptor and with an antagonist of the G(alpha)i-and/or G(alpha)o-coupled receptor;

(D) measuring the cytoplasmic $Ca^{2+}$ concentration of the cells; and (E) comparing the results from the measurements of steps (B) and (D);

wherein the amount of the agonist of the G(alpha)q-coupled receptor that gives a sub-threshold activity is that amount at which the ratio of:

(i) the result of the measurement of the cytoplasmic $Ca^{2+}$ concentration of the cells on treatment with an amount of the agonist of the G(alpha)q-coupled receptor to (ii) the result of the measurement of the cytoplasmic $Ca^{2+}$ concentration of the cells on simultaneous treatment of the cells with the same amount of the agonist of the G(alpha)q-coupled receptor and an amount of an agonist of the G(alpha)i- and/or G(alpha)o-coupled receptor that is sufficient for complete activation, does not exceed about 1:20.

18. A method of identifying antagonists of a G(alpha)i- and/or G(alpha)o-coupled receptor, said method comprising:

(I) providing cells that express the G(alpha)i- and/or G(alpha)o-coupled receptor and at least one G(alpha)q-coupled receptor; and (II) carrying out steps (A) to (E) of the method according to claim 17, wherein a test substance, whose activity in respect of the G(alpha)i- and/or G(alpha)o-coupled receptor is to be tested is used as the antagonist of the G(alpha)i- and/or G(alpha)o-coupled receptor in step (C).

19. A method according to claim 17, wherein before step (A) the amount of the agonist of the G(alpha)q-coupled receptor that gives a sub-threshold activity is determined by:

(1) treating the cells with different amounts of the agonist of the G(alpha)q-coupled receptor;

(2) measuring the cytoplasmic $Ca^{2+}$ concentration of the cells for each amount of the agonist of step (1);

(3) simultaneously treating the cells with different amounts of the agonist of the G(alpha)q-coupled receptor and with a constant amount of the agonist of the G(alpha)i- and/or G(alpha)o-coupled receptor sufficient for complete activation of the receptor;

(4) measuring the cytoplasmic $Ca^{2+}$ concentration of the cells for each amount of the agonist of the G(alpha)q-coupled receptor of step (3); and (5) comparing the results of the measurements of steps (2) and (4) for equal amounts of the agonist of the G(alpha)q-coupled receptor.

20. A method according to claim 19, wherein step (5) comprises calculating a ratio from the results of the measurements of steps (2) and (4).

21. A method according to claim 20, wherein the amount of the agonist of the G(alpha)q-coupled receptor is that amount at which a ratio of the result of the measurement of step (2) to the result of the measurement of step (4) of not more than about 1:20 is obtained.

22. A method according to claim 17, wherein the measurement of the cytoplasmic $Ca^{2+}$ concentration is carried out using a $Ca^{2+}$-dependent dye.

23. A method according to claim 22, wherein the dye is a fluorescent dye.

24. A method according to claim 23, wherein the fluorescent dye is selected from the group consisting of molecules of the families fura, indo, quin, coumarinbenzothiazoles, fluo, calcium green, Oregon green, calcium orange, calcium crimson, magnesium green, rhod and X-rhod.

25. A method according to claim 17, wherein the G(alpha)i- or G(alpha)o-coupled receptor is selected from the group consisting of opioid receptors, P2Y12, receptors of the Edg family, GABA-B, muscarine-M2, -M4, dopamine-D2, -D3, -D4, histamine-H3 receptors, receptors of the serotonin-H1 family, C3a, C5a, fMLP, CXCR1-5, CCR1-9, XCR1, CX3CR1, neuropeptide-Y1 to 6, somatostatin-Sst2 receptors, chemoattractant R-homologous molecule expressed on Th2 cells, prostaglandin-E type 3, adenosine-A1 and adenosine-A3 receptors.

26. A method according to claim 17, wherein the G(alpha)q-coupled receptor is selected from the group consisting of muscarine-M1, -M3, -M5, serotonin-H2, bombesin, cholecystokinin, neurokinin, prostaglandin-E type I, adenosine-A2B, P2Y1, P2Y2, P2Y4, P2Y6, P2Y11, calcitonin, mGluR1 receptors, angiotensin II receptor 1, protease activated receptor 1 and serotonin R.

27. A method according to claim 17, wherein at least one of the G(alpha)i-coupled receptor, the G(alpha)o-coupled receptor and the G(alpha)q-coupled receptor is expressed endogenously by the cells.

28. A method according to claim 3, wherein the cells have been transfected with a nucleic acid construct for expression of at least one receptor selected from the group consisting of the G(alpha)i-coupled receptor, the G(alpha)o-coupled receptor and the G(alpha)q-coupled receptor.

29. A method according to claim 17, wherein the cells are selected from the group consisting of stable cell lines, primary cell cultures and tissue cells.

30. A method according to claim 29, wherein the cell line is selected from the group consisting of CHO, HEK293, THP-1, SH-SY5Y, Jurkat, HeLa, L cells, A-10, Cos-7, NIH 3T3, ECV304, RBL, UMR 106, PC3, GH3, PC1 and IMR-32.

31. A method according to claim 17, wherein the agonist of the G(alpha)q-coupled receptor is selected from the group consisting of adenosine, AMP, ADP, ATP, uridine, UMP, UDP, UTP, cytosine, CMP, CDP, CTP, guanosine, GMP, GDP, GTP, thymidine, TMP, TDP, TTP, inosine, IMP, IDP and ITP and muscarine receptor agonists.

32. A method according to claim 17, wherein the agonist of the G(alpha)i- and/or G(alpha)o-coupled receptor is selected from the group consisting of GRT0777S, Damgo, fentanyl, serotonin and morphines.

33. A method according to claim 17, wherein the antagonist of the G(alpha)i- and/or G(alpha)o-coupled receptor is naloxone.

\* \* \* \* \*